United States Patent

Morimoto

(10) Patent No.: US 9,230,784 B2
(45) Date of Patent: Jan. 5, 2016

(54) MASS SPECTROMETER AND MASS SPECTROMETRY METHOD

(71) Applicant: SHIMADZU CORPORATION, Kyoto-shi, Kyoto (JP)

(72) Inventor: Kentaro Morimoto, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 14/565,479

(22) Filed: Dec. 10, 2014

(65) Prior Publication Data

US 2015/0219606 A1  Aug. 6, 2015

(30) Foreign Application Priority Data

Feb. 5, 2014  (JP) ................. 2014-020235

(51) Int. Cl.
H01J 49/34 (2006.01)
H01J 49/02 (2006.01)
H01J 49/00 (2006.01)
G01N 30/72 (2006.01)

(52) U.S. Cl.
CPC ........ H01J 49/0036 (2013.01); G01N 30/7233 (2013.01)

(58) Field of Classification Search
CPC .............. H01J 49/0027; H01J 49/0031; H01J 49/0036; H01J 49/004; H01J 49/26
USPC ........................ 250/281, 282, 286, 299, 300
See application file for complete search history.

(56) References Cited

U.S. PATENT DOCUMENTS

| | | | | |
|---|---|---|---|---|
| 2004/0195500 | A1* | 10/2004 | Sachs et al. | 250/282 |
| 2006/0289735 | A1* | 12/2006 | Ohtake et al. | 250/282 |
| 2007/0211928 | A1* | 9/2007 | Weng et al. | 382/128 |
| 2009/0215103 | A1* | 8/2009 | Gorenstein et al. | 435/24 |

FOREIGN PATENT DOCUMENTS

JP  2012-251878 A  12/2012

\* cited by examiner

*Primary Examiner* — Nicole Ippolito
*Assistant Examiner* — David E Smith
(74) *Attorney, Agent, or Firm* — Sughrue Mion, PLLC

(57) ABSTRACT

There are provided a mass spectrometer and a mass spectrometry method which can realize shortening of the measurement time and reduction of the consumption of a sample. Ions, in which the intensity distribution forms a peak waveform at both of each retention time and each mass-to-charge ratio (peaks P11, P21, P22 and P32) are detected as MS/MS precursor ions based on three-dimensional information of a retention time, a mass-to-charge ratio and an intensity. Whether or not $MS^3$ analysis is performed for each ion is determined beforehand based on whether or not the isotopic distributions of a plurality of ions are superimposed at each retention time rt1 to rt3. Ions (peaks P21 and P22) for which $MS^3$ analysis is performed and ions (peaks P11 and P32) for which $MS^3$ analysis is not performed can be hereby determined at the time the MS spectrum is measured to detect MS/MS precursor ions.

2 Claims, 7 Drawing Sheets

MASS SPECTROMETER AND MASS SPECTROMETRY METHOD

BACKGROUND OF THE INVENTION

1. Field of the Invention

The present invention relates to a mass spectrometer and a mass spectrometry method in which sample components separated by a liquid chromatograph are ionized, and the obtained ions are cleaved and subjected to mass spectrometry to perform $MS^n$ analysis (n is an integer of 3 or greater).

2. Description of the Related Art

Sample components may be identified based on a $MS^n$ spectrum obtained by separating sample components by a liquid chromatograph and sequentially subjecting the separated sample components to $MS^n$ analysis in identification of an organism-derived high-molecular compound such as a peptide. In this case, mass spectrometry (MS analysis) of an ionized sample component is first performed to measure a MS spectrum. The measured MS spectrum is then correlated with a retention time to obtain three-dimensional information of a retention time (RT), a mass-to-charge ratio (m/z) and an intensity (I).

FIG. 8 is a view showing one example of three-dimensional information of a retention time, a mass-to-charge ratio and an intensity obtained from MS analysis. In this example, peaks of mass-to-charge ratios mz1 and mz2 are detected in MS spectra of mutually adjacent retention times rt1 to rt3. The intensity of the mass-to-charge ratio mz2 is low at the retention time rt1, and the mass-to-charge ratio mz1 is low at the retention time rt3.

In this case, ions corresponding to the peak P11 of the mass-to-charge ratio mz1 for the retention time rt1, the peak P21 of the mass-to-charge ratio mz1 and the peak P22 of the mass-to-charge ratio mz2 for the retention time rt2, and the peak P32 of the mass-to-charge ratio mz2 for the retention time rt3 are detected as MS/MS precursor ions. Thereafter, at each retention time, the MS/MS precursor ion is cleaved and subjected to mass spectrometry (MS/MS analysis) to measure a MS/MS spectrum. Sample components can be identified by performing search using a known database based on the MS/MS spectra obtained as described above.

However, for example, when a peptide as a sample component is subjected to post-translation modification, or ions are not sufficiently cleaved in MS/MS analysis, sample components may not be identified by database search as described above. In this case, it is effective that after MS/MS analysis is performed, a $MS^3$ precursor ion is further detected from the MS/MS spectrum, and the $MS^3$ precursor ion is cleaved and subjected to mass spectrometry ($MS^3$ analysis) to measure a $MS^3$ spectrum (see JP-A-2012-251878).

When database search is performed based on a MS spectrum, a MS/MS spectrum and a $MS^3$ spectrum that are obtained by performing analyses up to $MS^3$ analysis, identification results can be obtained with higher reliability.

However, when $MS^3$ precursor ions are detected from all MS/MS spectra obtained by MS/MS analysis and $MS^3$ analysis is performed, there is the problem that the measurement time is prolonged and the consumption of a sample is increased.

The present invention has been devised in view of the above-described situations, and an object of the present invention is to provide a mass spectrometer and a mass spectrometry method which can realize shortening of the measurement time and reduction of the consumption of a sample.

SUMMARY OF THE INVENTION

A mass spectrometer of the present invention is a mass spectrometer in which sample components separated by a liquid chromatograph are ionized, and the obtained ions are cleaved and subjected to mass spectrometry to perform $MS^n$ analysis (n is an integer of 3 or greater), the mass spectrometer including a MS measurement processing section, an ion detection processing section, a superimposition determination processing section and an execution determination processing section. The MS measurement processing section is configured to measure a MS spectrum which represents a relation of a mass-to-charge ratio and an intensity by performing mass spectrometry of the ionized sample components. The ion detection processing section is configured to detect, as a MS/MS precursor ion, an ion, the intensity distribution of which forms a peak waveform at both of each retention time and each mass-to-charge ratio, based on three-dimensional information of a retention time, a mass-to-charge ratio and an intensity, which is obtained by correlating the MS spectrum with the retention time. The superimposition determination processing section is configured to determine whether or not isotopic distributions of a plurality of ions detected as MS/MS precursor ions are superimposed at each retention time. The execution determination processing section is configured to determine whether or not $MS^3$ analysis is performed for each ion detected as a MS/MS precursor ion, based on the result of determination by the superimposition determination processing section.

According to this configuration, whether or not $MS^3$ analysis is performed for ions detected as MS/MS precursor ions can be determined beforehand based on whether isotopic distributions of a plurality of ions detected as MS/MS precursor ions are superimposed at each retention time. Ions for which $MS^3$ analysis is performed and ions for which $MS^3$ analysis is not performed can be hereby determined at the time when the MS spectrum is measured to detect MS/MS precursor ions.

Therefore, ions for which it is determined that $MS^3$ analysis is not performed can be subjected to analyses up to MS/MS analysis, and ions for which it is determined that $MS^3$ analysis is performed can be subjected to MS/MS analysis and $MS^3$ analysis in succession. Therefore, the measurement time can be shortened and the consumption of a sample can be reduced as compared to a conventional configuration in which $MS^3$ precursor ions are detected from all MS/MS spectra obtained by MS/MS analysis and $MS^3$ analysis is performed.

A mass spectrometry method of the present invention is a mass spectrometry method in which sample components separated by a liquid chromatograph are ionized, and the obtained ions are cleaved and subjected to mass spectrometry to perform $MS^n$ analysis (n is an integer of 3 or greater). The method includes: measuring a MS spectrum which represents a relation of a mass-to-charge ratio and an intensity by performing mass spectrometry of the ionized sample components; detecting, as a MS/MS precursor ion, an ion, the intensity distribution of which forms a peak waveform at both of each retention time and each mass-to charge ratio, based on three-dimensional information of a retention time, a mass-to-charge ratio and an intensity, which is obtained by correlating the MS spectrum with the retention time; determining whether or not isotopic distributions of a plurality of ions detected as MS/MS precursor ions are superimposed at each retention time; and determining whether or not $MS^3$ analysis is performed for each ion detected as a MS/MS precursor ion, based on the result of determination by the superimposition determination step.

According to the present invention, ions for which it is determined that $MS^3$ analysis is not performed can be subjected to analyses up to MS/MS analysis, and ions for which it is determined that $MS^3$ analysis is performed can be subjected to MS/MS analysis and $MS^3$ analysis in succession, so that the measurement time can be shortened, and the consumption of a sample can be reduced.

DETAILED DESCRIPTION OF THE PREFERRED EMBODIMENTS

Figure 1:
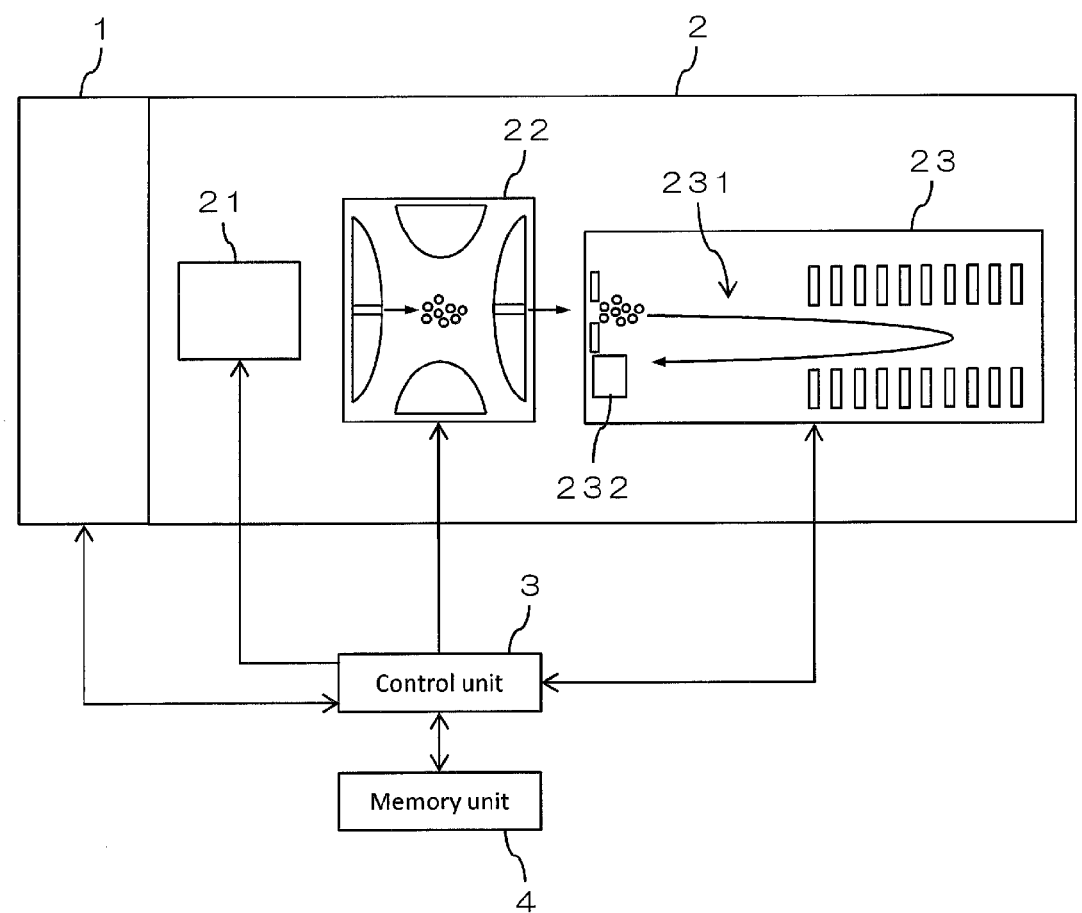
FIG. 1 is a schematic view showing an example of a configuration of amass spectrometer according to one embodiment of the present invention.

FIG. 1 is a schematic view showing an example of a configuration of amass spectrometer according to one embodiment of the present invention. The mass spectrometer according to this embodiment can be used in identification of an organism-derived high-molecular compound such as a peptide, and includes a liquid chromatograph 1, a mass spectrometry unit 2, a control unit 3, a memory unit 4, and so on.

The liquid chromatograph 1 includes a column (not illustrated) and has a known configuration. A sample supplied to the column of the liquid chromatograph 1 is separated for each sample component in the process of passing through the column, and sequentially guided to a mass spectrometry unit 2 in a vacuum state. Different spectra are hereby obtained according to a retention time.

The mass spectrometry unit 2 includes, for example, an ionization chamber 21, an ion trap 22 and a TOFMS (time of flight mass spectrometer) 23. Sample components separated by the liquid chromatograph 1 are supplied to the ionization chamber 21, and ionized using an ionization method such as ESI (electrospray ionization). It is to be noted that the method for ionizing sample components is not limited to EST, and various kinds of other methods such as APCI (atmospheric pressure chemical ionization) can be used.

The ion trap 22 is, for example, of a three-dimensional quadrupole type, and can capture ions obtained in the ionization chamber 21, and selectively leave some of the captured ions in the ion trap 22 and cleave the ions by CID (collision-induced dissociation). The ions cleaved in this manner are supplied to the TOFMS 23 from the ion trap 22.

In the TOFMS 23, ions flying in a flight space 231 are detected by an ion detector 232. Specifically, ions accelerated by an electric field formed in the flight space 231 are temporally separated according to a mass-to-charge ratio while flying in the flight space 231, and sequentially detected by the ion detector 232. A relationship between a mass-to-charge ratio and a detection intensity in the ion detector 232 is hereby measured as a spectrum to realize mass spectrometry.

In this embodiment, by repeatedly performing a series of operations in which ions are cleaved in the ion trap 22 and subjected to mass spectrometry by the TOFMS 23, $MS^n$ analysis (n is an integer of 3 or greater) can be performed to measure a $MS^n$ spectrum. Sample components can be identified by performing database search using $MS^n$ spectra obtained as described above.

The control unit 3 controls the operations of the liquid chromatograph 1 and the mass spectrometry unit 2, and processes a $MS^n$ spectrum obtained by mass spectrometry. The memory unit 4 includes, for example, a RAM (Random Access Memory), a ROM (Read Only Memory), a hard disk and so on, and stores data used for process in the control unit 3, data generated by process in the control unit 3, and so on. The control unit 3 and the memory unit 4 may be formed integrally with or separately from the liquid chromatography 1 and the mass spectrometry unit 2.

Figure 2:
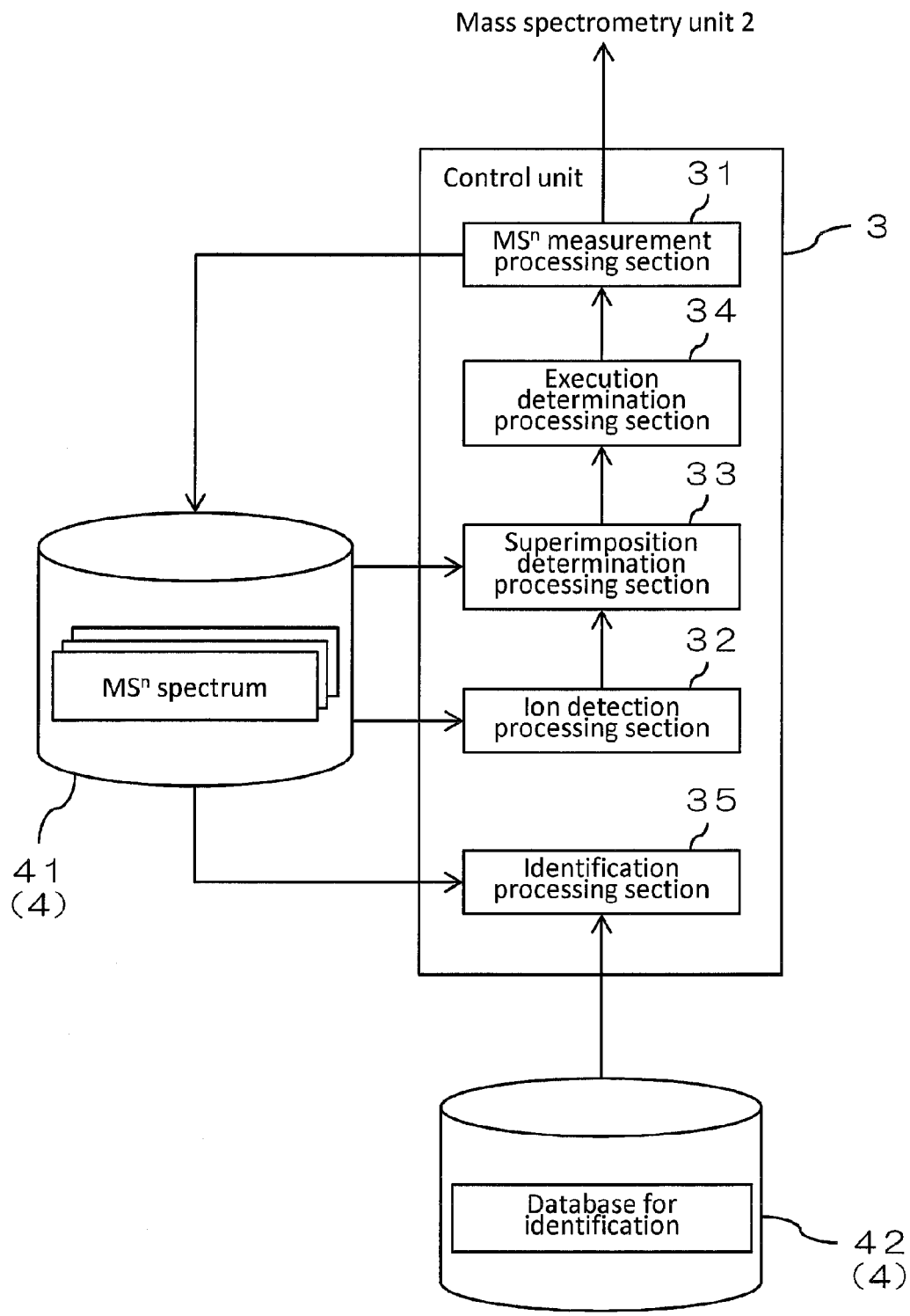
FIG. 2 is a block diagram showing one example of a control unit and a memory unit.

FIG. 2 is a block diagram showing one example of the control unit 3 and the memory unit 4. For example, the control unit 3 includes a CPU (Central processing Unit), and functions as a $MS^n$ measurement processing section 31, an ion detection processing section 32, a superimposition determination processing section 33, an execution determination processing section 34, an identification processing section 35 and so on, as the CPU runs a program.

The $MS^n$ measurement processing section 31 performs a process for measuring a $MS^n$ spectrum in the mass spectrometry unit 2. The measured $MS^n$ spectrum is stored in a spectrum storage region 41 assigned to the memory unit 4. In the $MS^n$ analysis, a MS spectrum, a MS/MS spectrum, a $MS^3$ spectrum ... are sequentially measured, and each is stored in the spectrum storage region 41.

The ion detection processing section 32 detects, based on a $MS^{n-1}$ spectrum, an ion ($MS^n$ precursor ion) that is a target at the time of measuring a $MS^n$ spectrum. In $MS^n$ analysis, mass spectrometry (MS analysis) of a sample ionized in the ionization chamber 21 is first performed in the TOFMS 23 to measure a MS spectrum. At this time, the $MS^n$ measurement processing section 31 functions as a MS measurement processing section. The ion detection processing section 32 then detects a MS/MS precursor ion based on the measured MS spectrum.

In this embodiment, a MS/MS precursor ion is detected based on three-dimensional information of a retention time (RT), a mass-to-charge ratio (m/z) and an intensity (I), which is obtained by correlating a MS spectrum with a retention time. At this time, an ion in which an intensity distribution forms a peak waveform having an intensity equal to or more than a predetermined value at both of each retention time and each mass-to-charge ratio is detected as a MS/MS precursor ion.

Figure 3:
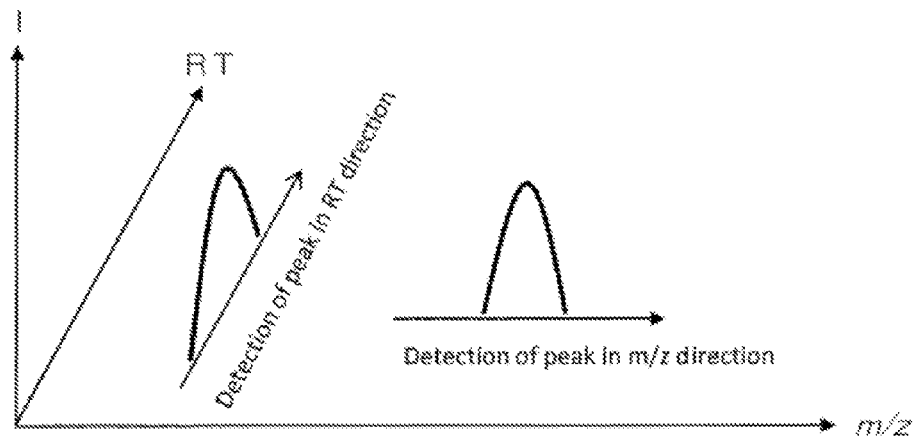
FIG. 3 is a view for explaining an aspect in detection of a MS/MS precursor ion based on three-dimensional information.

FIG. 3 is a view for explaining an aspect in detection of a MS/MS precursor ion based on three-dimensional information. In this embodiment, as shown in FIG. 3, peak detection is performed in both the retention time direction and mass-to-charge ratio direction based on three-dimensional information: a retention time (RT), a mass-to-charge ratio (m/z) and an intensity (I).

As a result, an ion corresponding to a peak that also forms a peak waveform at each retention time among peaks detected at each mass-to-charge ratio is detected as a MS/MS precursor ion. For example, in the example in FIG. 8, the peak P11 of the mass-to-charge ratio mz1 at the retention time rt1, the peak P21 of the mass-to-charge ratio mz1 and the peak P22 of the mass-to-charge ratio mz2 at the retention time rt2, and the peak P32 of the mass-to-charge ratio mz2 at the retention time rt3 each forms a peak waveform at both of each retention time and each mass-to-charge ratio.

Referring to FIG. 2 again, the superimposition determination processing section 33 determines whether or not isotopic distributions of a plurality of ions detected as MS/MS precursor ions are superimposed at each retention time. The isotopic distribution forms a waveform that depends on the composition of sample components to some extent, and therefore by using a known algorithm, whether or not a plurality of isotopic distributions are superimposed can be determined.

The execution determination processing section 34 determines whether or not $MS^3$ analysis is performed for each ion detected as a MS/MS precursor ion based on the result of determination by the superimposition determination processing section 33. Specifically, it is determined that not only MS/MS analysis but also $MS^3$ analysis is performed for MS/MS precursor ions in which isotopic distributions are mutually superimposed at each retention time. On the other hand, it is determined that $MS^3$ analysis is not performed for MS/MS precursor ions in which isotopic distributions are not mutually superimposed at each retention time.

In this way, whether or not analyses up to $MS^3$ analysis are performed for each MS/MS precursor ion is determined beforehand, and the $MS^n$ measurement processing section 31 performs MS/MS analysis and subsequent $MS^n$ analysis. The identification processing section 35 performs a process for identifying a sample component based on the measured $MS^n$ spectrum. The identification process may be configured to be automatically performed, or may be configured to be manually performed by a user.

In this example, a database for identification is assigned to a database region 42 that is a part of the memory unit 4. Sample components can be identified by calculating a degree of coincidence between data of the mass-to-charge ratio for various sample components, which is included in the database for identification, and the mass-to-charge ratio of each peak included in the $MS^n$ spectrum. It is to be noted that the database for identification is not necessarily configured to be assigned to the memory unit 4 of the mass spectrometer, and for example, a database connected to the mass spectrometer through a network can be used.

Figure 4:
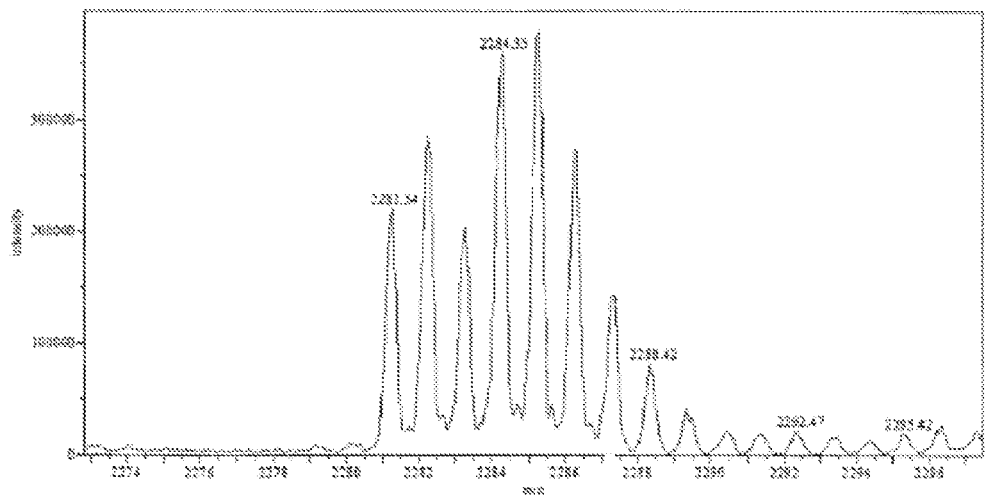
FIG. 4 is a view showing one example of a MS spectrum at a certain retention time.
Figure 5:
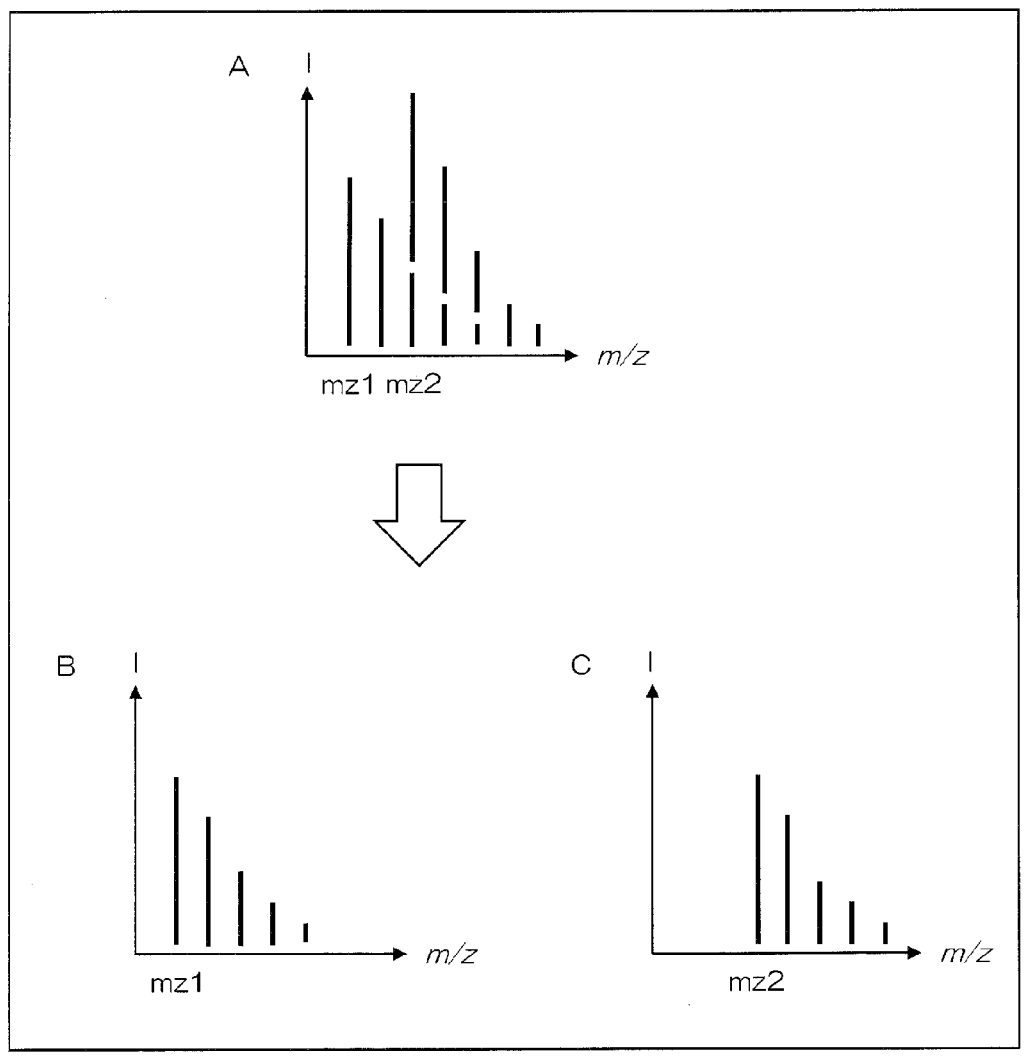
FIG. 5 is a view for explaining an aspect of a process by a superimposition determination processing section, and shows the MS spectrum of FIG. 4 in a simplified manner.

FIG. 4 is a view showing one example of a MS spectrum at a certain retention time. FIG. 5 is a view for explaining an aspect of a process by the superimposition determination processing section 33, and shows the MS spectrum of FIG. 4 in a simplified manner.

The example in FIG. 4 is a MS spectrum for two types of peptides obtained from a tryptic digest of ovalbumin. In this example, the peak of monoisotopic mass m/z=2281 and the peak of monoisotopic mass m/z=2284 are close to each other, and their isotopic distributions are mutually superimposed.

That is, when the MS spectrum of FIG. 4 is simplified as in FIG. 5A, the MS spectrum can be separated into an isotopic distribution of monoisotopic mass m/z=2281 as shown in FIG. 5B and an isotopic distribution of monoisotopic mass m/z=2284 as shown in FIG. 5C. In this case, it is determined that for an ion corresponding to monoisotopic mass m/z=2281 and an ion corresponding to monoisotopic mass m/z=2284, not only MS/MS analysis but also $MS^3$ analysis is performed because their isotopic distributions are mutually superimposed.

Figure 6:
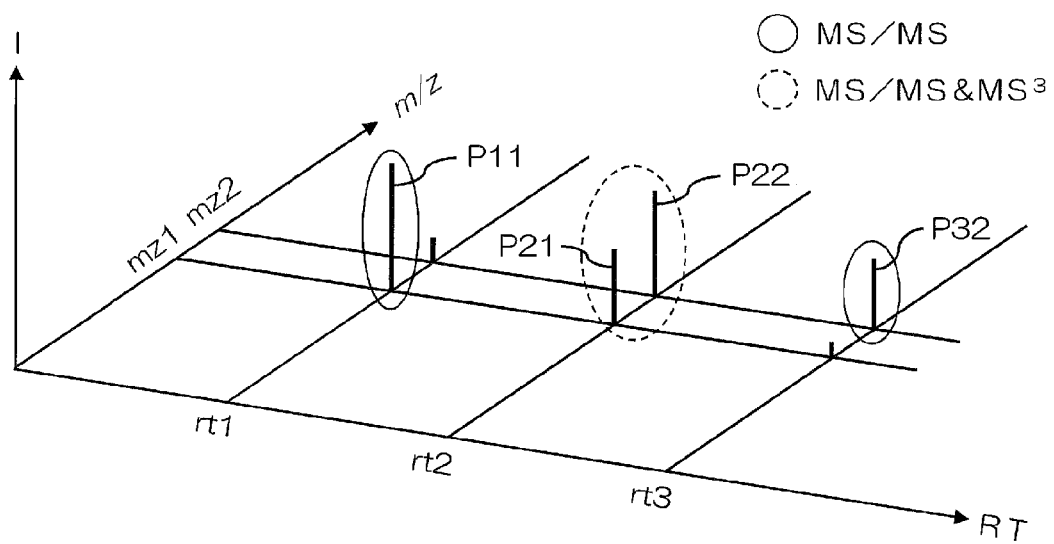
FIG. 6 is a view for explaining an aspect of a process by a execution determination processing section.
Figure 8:
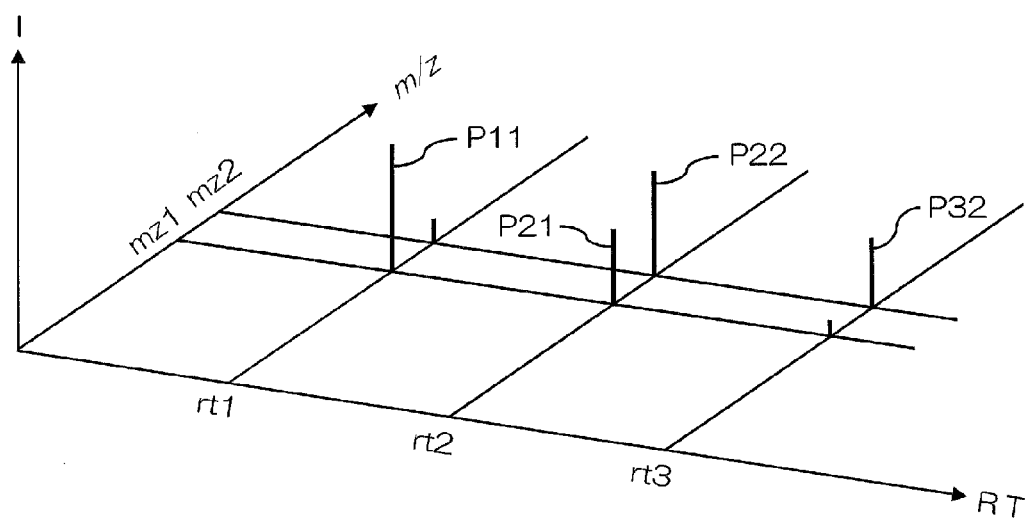
FIG. 8 is a view showing one example of three-dimensional information of a retention time, a mass-to-charge ratio and an intensity obtained from MS analysis.

FIG. 6 is a view for explaining an aspect of a process by the execution determination processing section 34. Here, a specific aspect of whether or not it is determined that the ion is subjected to $MS^3$ analysis for peaks P11, P21, P22 and P32 at each retention time rt1 to rt3 in the example in FIG. 8 is described.

In the case where like the peak P11 of the mass-to-charge ratio mz1 at the retention time rt1, adjacent peaks of the mass-to-charge ratio do not exist at the retention time rt1 and ions whose isotopic distributions are mutually superimposed do not exist, it is determined that $MS^3$ analysis is not performed and analyses up to MS/MS analysis are performed for an ion corresponding to the peak P11.

In the case where like the peak P21 of the mass-to-charge ratio mz1 and the peak P22 of the mass-to-charge ratio mz2 at the retention time rt2, adjacent peaks of the mass-to-charge ratio exist at the retention time rt2, whether or not their isotopic distributions are mutually superimposed is determined. In the case where as a result, the isotopic distributions of each peak P21 and P22 are mutually superimposed, it is determined that not only MS/MS analysis but also $MS^3$ analysis is performed for ions corresponding to the peaks P21 and P22.

In the case where like the peak P32 at the mass-to-charge ratio mz2 at the retention time rt3, adjacent peaks of the mass-to-charge ratio do not exist at the retention time rt3 and ions whose isotopic distributions are mutually superimposed do not exist, it is determined that $MS^3$ analysis is not performed and analyses up to MS/MS analysis are performed for an ion corresponding to the peak P32.

Thus, in this embodiment, whether or not $MS^3$ analysis is performed for ions detected as MS/MS precursor ions can be determined beforehand based on whether isotopic distributions of a plurality of ions (peaks P11, P21, P22 and P32) detected as MS/MS precursor ions are superimposed at each retention time rt1 to rt3. Ions (peaks P21 and P22) for which $MS^3$ analysis is performed and ions (peaks P11 and P32) for which $MS^3$ analysis is not performed can be hereby determined at the time when the MS spectrum is measured to detect MS/MS precursor ions.

Therefore, ions (peaks P11 and P32) for which it is determined that $MS^3$ analysis is not performed can be subjected to analyses up to MS/MS analysis, and ions (peaks P21 and P22) for which it is determined that $MS^3$ analysis is performed can be subjected to MS/MS analysis and $MS^3$ analysis in succession. Therefore, the measurement time can be shortened and the consumption of a sample can be reduced as compared to a conventional configuration in which $MS^3$ precursor ions are detected from all MS/MS spectra obtained by MS/MS analysis and $MS^3$ analysis is performed.

Figure 7:
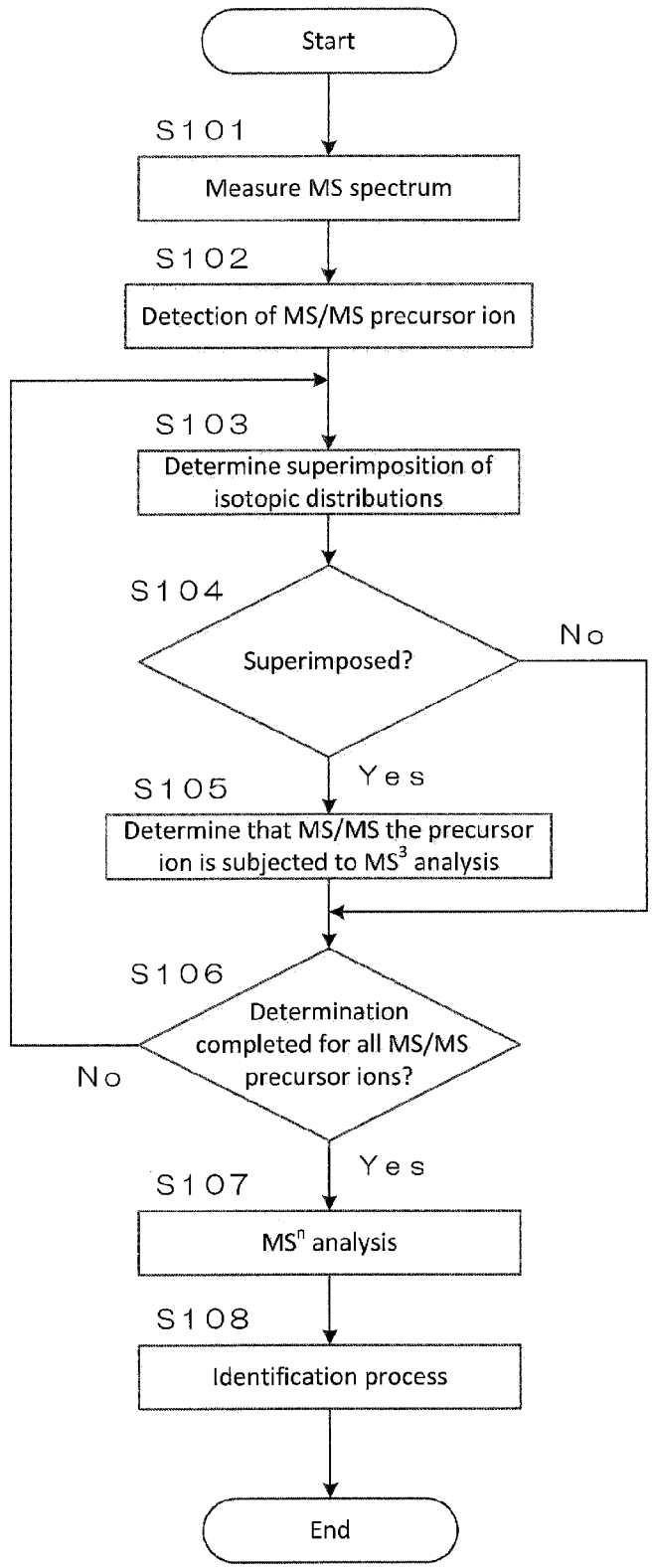
FIG. 7 is a flow chart showing one example of process by the control unit at the time of performing $MS^n$ analysis.

FIG. 7 is a flow chart showing one example of process by the control unit 3 at the time of performing $MS^n$ analysis. For performing $MS^n$ analysis, first, sample components separated by the liquid chromatograph 1 are sequentially ionized by the mass spectrometry unit 2, and mass spectrometry (MS analysis) of the ionized sample is performed to measure a MS spectrum (step S101: MS measurement step).

A MS/MS precursor ion is then detected based on three-dimensional information of a retention time, a mass-to-charge ratio and an intensity, which is obtained by correlating a measured MS spectrum with a retention time (step S102: ion detection step). Thereafter, whether or not isotopic distributions of each ion detected as a MS/MS precursor ion are superimposed at each retention time (step S103: superimposition determination step).

It is determined that ions whose isotopic distributions are mutually superimposed (Yes in step S104) as a result of the determination are to be subjected to $MS^3$ analysis (step S105), and therefore for these ions, not only MS/MS analysis but also $MS^3$ analysis is performed. On the other hand, it is determined that ions having no superimposed isotopic distributions (No in step S104) are not to be subjected to $MS^3$ analysis, and therefore for these ions, analyses up to MS/MS analysis are performed. Here, steps S104 and S105 constitute an execution determination step.

In this manner, the processes in steps S103 to S105 are performed for each MS/MS precursor ion, and after determination is completed for all the MS/MS precursor ions (Yes in step S106), the $MS^n$ measurement processing section 31 performs $MS^n$ analysis (n≥2) (step S107: $MS^n$ measurement step). At this time, for ions that are determined to be subjected to $MS^3$ analysis, not only MS/MS analysis but also $MS^3$ analysis is performed. On the other hand, for ions that are not determined to be subjected to $MS^3$ analysis, $MS^3$ analysis is not performed, and analyses up to MS/MS analysis are performed.

For ions which are subjected to analyses up to $MS^3$ analysis, mass spectrometry of $MS^4$ analysis and subsequent analyses may be performed. In this case, a configuration may be employed in which the execution determination processing section 34 determines whether or not $MS^4$ analysis and subsequent analyses are performed for each ion detected as a MS/MS precursor ion.

An identification process is then performed based on the measured $MS^n$ spectrum to identify sample components (step S108: identification step). At this time, for ions for which $MS^3$ analysis is not performed, and analyses up to MS/MS analysis are performed, an identification process is performed using a MS/MS spectrum. On the other hand, for ions for which analyses up to $MS^3$ analysis are performed, an identification process with higher reliability is performed using both a MS/MS spectrum and a $MS^3$ spectrum.

In the embodiment described above, mass spectrometry is performed using the TOFMS 23. However, the present invention is not limited to such a configuration, and a configuration may be employed in which mass spectrometry is performed using other mass spectrometers such as a magnetic sector type mass spectrometer, a quadrupole mass spectrometer and a Fourier transform ion cyclotron resonance mass spectrometer, or a configuration may be employed in which mass spectrometry is performed using the mass separation function of the ion trap 22 itself.

The present invention is not limited to a configuration in which ions are cleaved using the ion trap 22, and a configuration may be employed in which ions are cleaved using the mass spectrometry unit 2 having a different configuration, such as a triple-quadrupole type mass spectrometry unit.

What is claimed is:

1. A mass spectrometer in which sample components separated by a liquid chromatograph are ionized, and the obtained ions are cleaved and subjected to mass spectrometry to perform $MS^n$ analysis (n is an integer of 3 or greater), the mass spectrometer comprising:

a MS measurement processing section configured to measure a MS spectrum which represents a relation of a mass-to-charge ratio and an intensity by performing mass spectrometry of the ionized sample components;

an ion detection processing section configured to detect, as a MS/MS precursor ion, an ion, the intensity distribution of which forms a peak waveform at both of each retention time and each mass-to-charge ratio, based on three-dimensional information of a retention time, a mass-to-charge ratio and an intensity, which is obtained by correlating the MS spectrum with the retention time;

an overlap determination processing section configured to determine whether or not isotopic distributions of a plurality of ions detected as MS/MS precursor ions have overlapping m/z ranges at each retention time; and an execution determination processing section configured to determine whether or not $MS^3$ analysis is performed for each ion detected as a MS/MS precursor ion, based on the result of determination by the overlap determination processing section.

2. A mass spectrometry method in which sample components separated by a liquid chromatograph are ionized, and the obtained ions are cleaved and subjected to mass spectrometry to perform $MS^n$ analysis (n is an integer of 3 or greater), the method comprising:

measuring a MS spectrum which represents a relation of a mass-to-charge ratio and an intensity by performing mass spectrometry of the ionized sample components;

detecting, as a MS/MS precursor ion, an ion, the intensity distribution of which forms a peak waveform at both of each retention time and each mass-to charge ratio, based on three-dimensional information of a retention time, a mass-to-charge ratio and an intensity, which is obtained by correlating the MS spectrum with the retention time;

determining whether or not isotopic distributions of a plurality of ions detected as MS/MS precursor ions have overlapping m/z ranges at each retention time; and determining whether or not $MS^3$ analysis is performed for each ion detected as a MS/MS precursor ion, based on the result of determination by the overlap determination step.

* * * * *